United States Patent [19]
Dory

[11] Patent Number: 6,028,547
[45] Date of Patent: Feb. 22, 2000

[54] METHOD AND DEVICE FOR PROCESSING SIGNALS REPRESENTATIVE OF WAVES REFLECTED, TRANSMITTED OR REFRACTED BY A VOLUME STRUCTURE WITH A VIEW TO EXPLORING AND ANALYZING THIS STRUCTURE

[76] Inventor: Jacques Dory, Le Moulin Brûlé—rue du Bas de Villiers, 77580 Villiers sur Morin, France

[21] Appl. No.: 09/061,105

[22] Filed: Apr. 16, 1998

[30] Foreign Application Priority Data

Apr. 18, 1997 [FR] France .................................. 97 04936

[51] Int. Cl.$^7$ .................................................. G01S 13/89
[52] U.S. Cl. ........................... 342/22; 342/127; 342/179; 342/195; 73/625
[58] Field of Search .................................. 342/22, 27, 90, 342/102, 126, 127, 179, 180, 194, 195, 197; 367/87; 73/618, 620, 625

[56] References Cited

U.S. PATENT DOCUMENTS

| | | | |
|---|---|---|---|
| 3,611,369 | 10/1971 | Maguire | 342/91 |
| 4,012,952 | 3/1977 | Dory | 73/67.7 |
| 4,317,369 | 3/1982 | Johnson | 73/607 |
| 4,430,653 | 2/1984 | Coon et al. | 342/22 |
| 4,717,916 | 1/1988 | Adams et al. | 342/107 |
| 4,817,434 | 4/1989 | Anderson | 73/625 |
| 4,836,026 | 6/1989 | P'an et al. | 73/62 |
| 4,841,489 | 6/1989 | Ozaki et al. | 367/7 |
| 4,852,577 | 8/1989 | Smith et al. | 600/443 |
| 5,269,307 | 12/1993 | Fife et al. | 600/447 |
| 5,384,573 | 1/1995 | Turpin | 342/179 |
| 5,673,050 | 9/1997 | Moussally et al. | 342/22 |
| 5,675,550 | 10/1997 | Ekhaus | 367/7 |
| 5,736,958 | 4/1998 | Turpin | 342/179 |
| 5,751,234 | 5/1998 | Turpin | 342/179 |
| 5,796,363 | 8/1998 | Mast | 342/22 |
| 5,806,521 | 9/1998 | Morimoto et al. | 600/447 |

OTHER PUBLICATIONS

M.I. Skolnik—"Introduction to Radar Systems" 1981 McGraw–Hill, U.S.A. XP002054016, p. 388, Para.10.7–p. 392.

*Primary Examiner*—John B. Sotomayor
*Attorney, Agent, or Firm*—William A. Drucker

[57] ABSTRACT

To explore and analyze the structure of an object (O), the method according to the invention comprises transmission of at least one incident wave into said structure, reception of the waves retransmitted by the structure, by a plurality of independent detection elements (D1, Dn); memorization after digitization of the data supplied by the detection elements, in a field memory (MC); in respect of each point (Pij) of the object (O), computation of the positions occupied, in the field memory by the signals detected by the detection elements (D1, Dn) corresponding to the waves coming from said point (Pij); then reading of the field memory and addition of all the values contained in the memory positions corresponding to each point (Pij), the value (Vp) representative of the importance of the wave coming from said point (Pij) being obtained by multiplying the result of the addition by a correction factor (K).

25 Claims, 4 Drawing Sheets

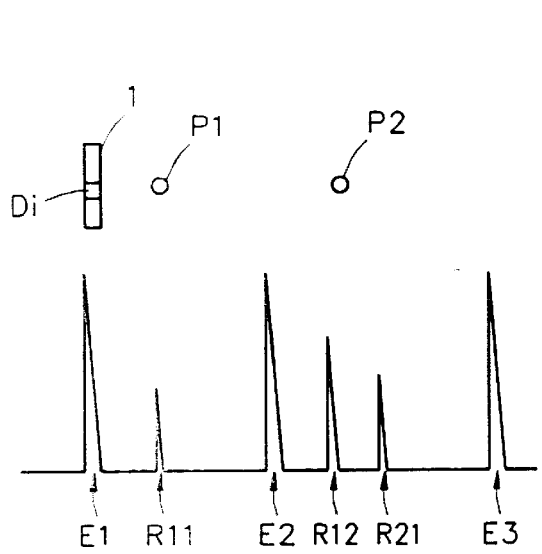
Fig. 6
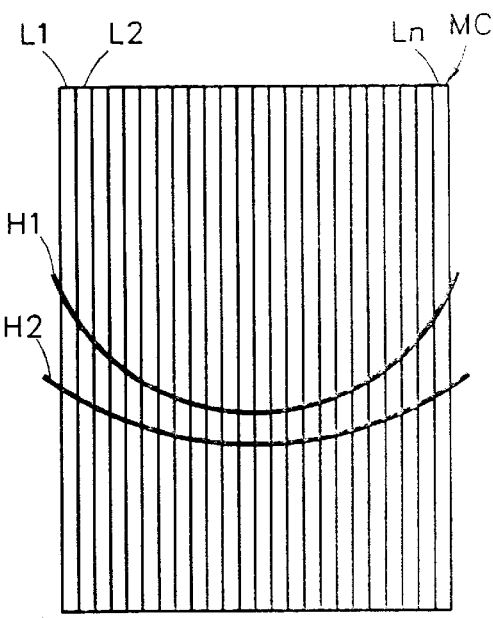
Fig. 7
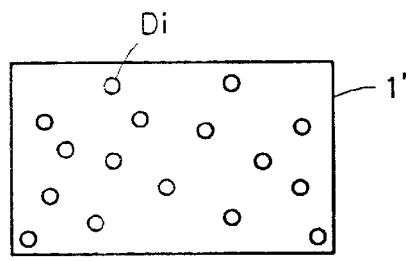
Fig. 9
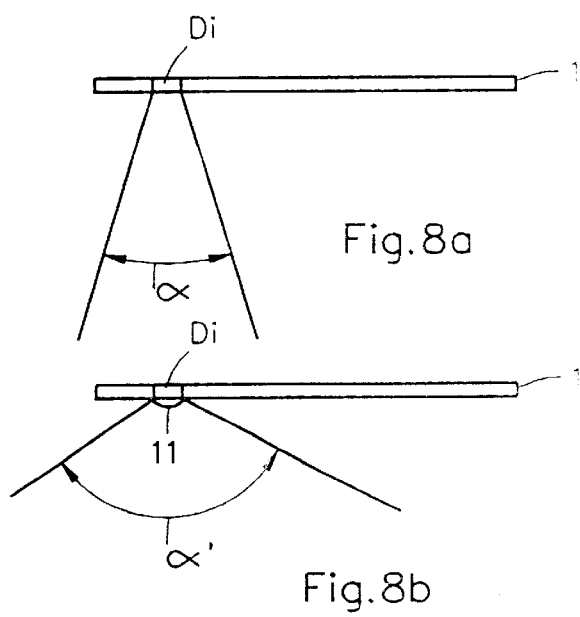
Fig. 8a
Fig. 8b

METHOD AND DEVICE FOR PROCESSING SIGNALS REPRESENTATIVE OF WAVES REFLECTED, TRANSMITTED OR REFRACTED BY A VOLUME STRUCTURE WITH A VIEW TO EXPLORING AND ANALYZING THIS STRUCTURE

BACKGROUND OF THE INVENTION

1. Field of the Invention

This invention relates to a method and device for processing signals representative of waves reflected, transmitted or refracted by a volume structure with a view to exploring and analyzing said structure.

It applies notably, though not exclusively, to the manufacture of equipment such as echo sounding apparatus, non-destructive testing instruments, sonar or even radar equipment.

2. Description of the Prior Art

Conventional instruments of this type usually use transmission means which transmit an incident wave into the medium or environment to be examined, and reception means, that may use all or part of the transmission means (homodyne systems), which receive the incident waves reflected by the structures encountered by the incident wave. Another means is also provided to transform and process the signals received by the reception means and to present them in a form that can be used by the user, e.g. in the form of an image enabling location of the position of the obstacles causing the incident wave to be reflected.

The method most widely used to obtain these results consists in using pulsed waves according to a process consisting in transmitting a pulse in a given direction (shot), in detecting the return of the echoes, in measuring the time lapsed between the transmission and reception and in deducing the distance and therefore the position of the obstacle that generated each echo. This shooting process is repeated for different directions, according to a predetermined scanning law.

Once this scanning has been performed, it then become possible to produce images, e.g. on a conventional display system, showing the obstacles detected by the echoes and whose positions are now known.

Numerous instruments of this type use the so-called "sequential" method by way of which the structure is examined line by line by means of a mobile beam, the exploration line being moved between shots.

In these conditions, the speed of examination increases with the cross-section of the exploring beam and the pulse rate. However, it so happens that the cross-section of the beam is limited by the spatial resolution required, whereas the pulse rate is limited by the time needed for all the reflected echoes to return to the probe.

To take an example, in order to examine an aluminum plate in which we are seeking to detect flaws of 1 mm in diameter, with a resolution of 3 mm, the cross-section of the beam may hardly exceed 2 mm, and the pulse rate must be below 1000 Hz in view of the reverberation phenomenon.

In these conditions, the surface examination speed cannot exceed 2 mm×2 mm×1000=4000 mm$^2$ per second, i.e. $4/1000$ths of a square meter, this being the equivalent of $4/1000$ths×3600=14.4 m$^2$ per hour. At the end of the production chain, this speed is often too slow insofar as it slows down production, whence the need to operate several installations in parallel.

In numerous other applications (pipe checking, rails on track, etc.), this limitation is even more critical.

With a view to remedying these drawbacks, it has already been proposed that there be transmitted, towards an object to be explored, a substantially plane wave of relatively large cross-section and generated by a probe constituted by a network comprising a plurality of transmission/reception units of small size, preferably less than one wavelength, in order to have a very large radiation pattern; these transmission units being attacked simultaneously, in parallel. From the point of view of reception, each transmission/reception unit operates independently, therefore receiving separately the waves reflected by the obstacles intercepting the beam located in its reception zone. After digitization, the data supplied by these transmission units (field of reflected waves) are stored in memories which are read in the opposite direction to that of write operations therein.

The read signals are then applied to a device for reconstituting the field of reflected waves, said device comprising a plurality of transmission units distributed according to a structure similar to that of the transmission/reception units of said probe. The read signals are applied to these transmission units in correspondence with the transmission, to the memory, of the write signals by the transmission/reception units.

The purpose of the reconstitution device is to reproduce, in an auxiliary environment, the reflected wave field in order to reproduce an image of the object, with a resolution which depends on the wavelength of the incident wave and on the dimensions of the probe elements.

In the case of the incident wave being an ultrasonic wave, the simplest solution is to form the image in an optically transparent environment and to view it by Schlieren's method.

However, this method does not readily lend itself to industrial use. Moreover, it is not linear and does not enable the rendering of high frequency components.

According to another method, the image is received on a third probe and the reading frequency is modulated so that the image of a structure is also focused when the corresponding signals arrive on this probe.

Experience has proved this system to be complex and that it requires probes with a very wide band. Furthermore, the signal becomes deteriorated after passing through three successive probes. In addition, further difficulties arise when the transmission wave is curved or circular.

OBJECT OF THE INVENTION

The main object of this invention is to remedy the preceding disadvantages.

SUMMARY OF THE INVENTION

To this end, it is based on the observation that, in a process such as the one described above, each point of the object to be explored gives rise to a wave which is memorized in field memory addresses distributed in the form of an arc of a hyperbola whose characteristics depend on the position of the point in relation to the probe and on the radiation pattern of each element (this hyperbola being theoretically reduced to the two asymptotes in the case of points situated against the probe).

In the event of a liquid relay being interposed between the probe and the part to be monitored (control by immersion), the waves memorized are distributed over curves which are not necessarily hyperbolae, as the path of the waves is more complex due to the refraction between the different propagation media. A similar phenomenon occurs when the material probed is not homogeneous from the point of view of speed of propagation. The term "hyperbola" will be used hereinafter to designate all these curves in a general manner.

Thus, the method according to the invention consists, on the one hand, in computing, for each point of the object to be explored, the read addresses in the field memory at which the data concerning the wave reverberated by this point are stored, these addresses being distributed in the field memory according to a law of hyperbolic distribution depending on the position of the point in relation to the probe, and, on the other hand, in rereading the field memory in accordance with each distribution law so as to obtain the data concerning the wave reverberated by the corresponding point of the object, and in having the result of a calculation performed on these data correspond to this point.

All the lines of the field memory, i.e. the zones containing the data relating to the signals respectively transmitted by the reception zones, are reread in parallel and the values are subjected to a mathematical operation, e.g. an addition (either directly in digital form or in analog form after a digital-to-analog conversion) to generate a value Vp. If the signal has been subjected to a logarithmic amplification, this addition corresponds to an original multiplication of the signal.

The value Vp is inserted into an image memory comprising a plurality of points to each of which corresponds a field memory reading law (e.g. hyperbolic), whose parameters depend on the coordinates of said point.

Given the fact that it takes too long to compute the reading law for each point in real time, this computation is performed beforehand and the results of this computation are stored in address memories associated with each line of the field memory.

The read process takes place as follows:

For each point of the image memory, the corresponding coordinates are transmitted in parallel to all the address memories. The latter immediately supply, in parallel the address of each field memory line enabling the corresponding reading law (e.g. hyperbolic) to be generated. The corresponding value Vp is then memorized in the image memory at the address of said point.

This method enables a quality image to be obtained rapidly when the field memory addresses corresponding to a point of the structure to be analyzed are read in parallel. However, when the number of points on the structure susceptible of reverberating a wave is much greater than the number of detection elements, artifacts appear on the image produced due to the fact that the field reverberated by the structure is under-sampled.

In theory, an ultrasonic pulse always comprises several oscillations, and the signal alternately becomes positive and negative, as a result of which the continuous component is nil. In these conditions, it is easy to show that if the field memory read addresses corresponding to a given point of the structure analyzed do not coincide exactly with the hyperbolic distribution of the addresses actually containing the signals corresponding to the waves retransmitted by this point, these read addresses successively contain positive and negative data of which the sum is zero. However, this is only rigorously true if the following conditions are fulfilled:

1. the detection elements are sufficiently numerous and close to one another (spatial sampling), and 2. the sampling frequency is high in relation to the frequency of ultrasounds, in order to obtain a large number of sampling levels (temporal sampling).

Otherwise, a non-zero value can be obtained for points in an empty zone of the structure under analysis.

The solution consisting in increasing the number of detection elements and in bringing them closer together requires a voluminous and costly device which precludes the use of matrix probes which would require a very large quantity of detection elements and therefore very powerful memories.

To remedy this drawback, the invention proposes to apply a correction factor to the result of the calculation performed on the data read in the field memory according to the distribution law corresponding to the wave reverberated by each point of the object.

Advantageously, this weighting factor varies as a function of the relation between the number of non-zero values read in the field memory and the theoretical maximum number of these non-zero values.

Moreover, in order to maintain good resolution, each detection element must have a very open radiation pattern which generally implies that the elements must be of very small size, preferably smaller than one wavelength. However, if there are few elements, the total reception area is also small, whence a loss of sensitivity that may be incompatible with the analysis to be carried out.

According to the invention, the detection elements can be of size greater than one wavelength and are all equipped with a means for increasing their aperture, and this means can consist of a miniature lens or a spherical cap.

BRIEF DESCRIPTION OF THE DRAWINGS

Further features and advantages of the invention will be apparent from an embodiment of the device according to the invention described, by way of a non-limiting example, in reference to the corresponding accompanying drawings in which:

FIG. 6 illustrates a sample distribution over time of echoes transmitted and received by a detection element, coming from two points situated at different distances from the probe;

FIG. 7 shows the distribution, in the memory, of the echoes reverberated by the two points represented in FIG. 6;

FIGS. 8a and 8b schematically represent the probe and the radiation pattern of a detection element, respectively according to the prior art and according to the invention;

FIG. 9 represents a matrix probe according to the invention.

DESCRIPTION OF THE PREFERRED EMBODIMENTS

Figure 1:
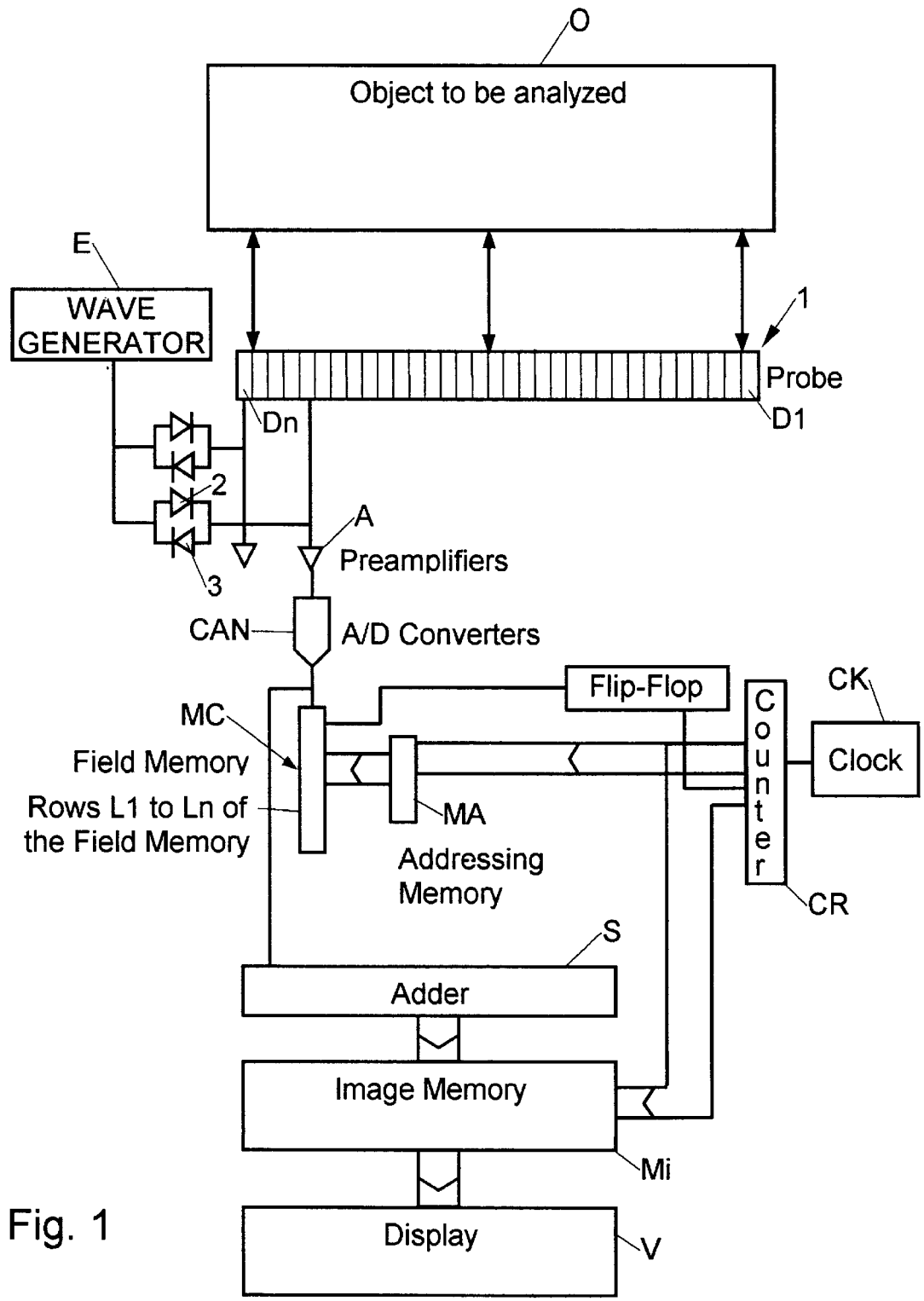
FIG. 1 is a theoretical diagram of a device for exploring and analyzing a volume structure.

The device represented in FIG. 1 can be used in ultrasonic devices using pulse reflection, for the purpose of non-destructive monitoring of materials or medical imagery.

It uses a probe 1 constituted by a linear strip comprised of a plurality of transmitter/receiver units $D_1$ to $D_n$ of small dimension (1 mm), numbering e.g. 128. Accordingly, the same probe 1 is used for both transmission and reception.

Each unit $D_1$ to $D_n$ is connected, on the one hand, to a zone, in this instance a respective line $L_1 \ldots L_n$ of a field memory MC, via a preamplifier A and an analog-to-digital converter CAN, and, on the other hand, to a transmitter E, via two diodes 2, 3 mounted head-to-foot and with a conduction threshold e.g. of the order of a fraction of a volt.

Thus, when the transmitter E transmits while supplying a voltage that can be as high as some one hundred volts AC, the diodes 2, 3 associated with all the transmitter/receiver units $D_1$ to $D_9$ are indeed highly conductive and behave as short-circuits, as a result of which all the units $D_1$ to $D_9$ are excited in parallel by the transmitter E and therefore produce a plane wave.

Conversely, at reception, each unit $D_1$ to $D_9$ operates independently and attacks the preamplifier A to which it is connected. In fact, the signals detected by the units are weak signals (a few dozen millivolts).

This arrangement has the further advantage of reducing input noise by isolating the preamplifiers A from the transmission circuit.

Each preamplifier A then attacks a corresponding analog-to-digital converter CAN and the digitized signals are stored in lines $L_1$ to $L_n$ of the field memory MC at write addresses supplied by an addressing memory MA itself addressed by a counter CR driven by a clock CK This counter CR and this clock CK are common to the addressing memory MA and to the field memory MC.

During write operations in the field memory MC, the lines $L_1$ to $L_n$ are addressed in parallel directly by the counter CR They can also be addressed independently to allow e.g. for a particular arrangement of the probe elements or form of the beam transmitted.

Advantageously, the number No of memory positions used during the write operation is chosen from among the powers of two, i.e. 512, 1024, etc.

If No is equal to e.g. 512, the positions 0 to 511 of the field memory are written.

Immediately subsequent to the write operation, the memories $L_1$ to $L_n$ are switched to the read position by means of a flip-flop B controlled by bit 10 of the counter CR.

From address 512 onwards, the addressing memory MA is addressed by the counter CR and thus applies simultaneously the addresses of the positions to be read in lines $L_1$ to $L_n$ of the field memory, in order to determine the value of each point P'ij of the image to build. Addresses contained in the addressing memory MA are computed so that the addressed memory positions follow a predetermined curve (read hyperbola).

Figure 2:
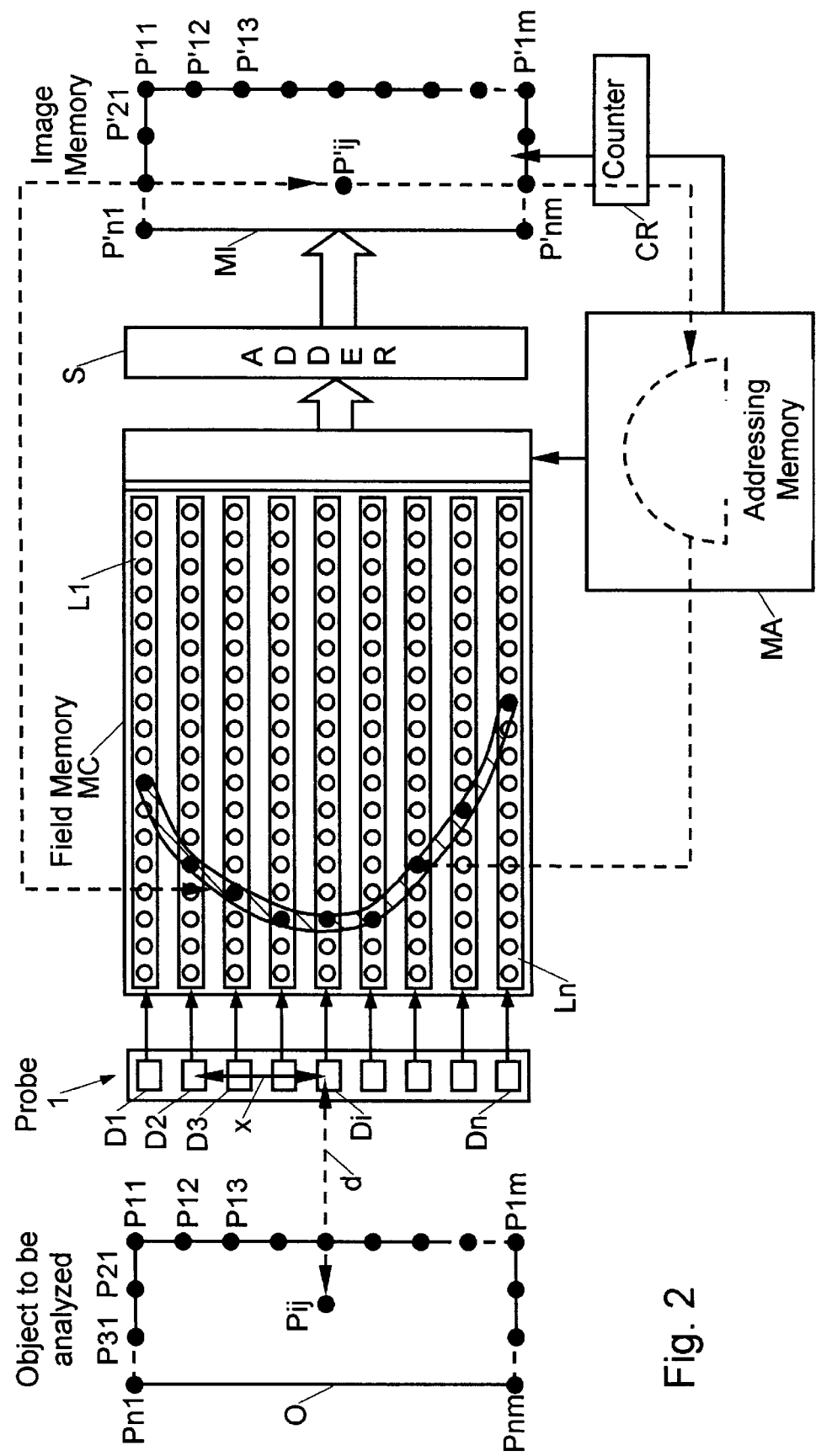
FIG. 2 is a schematical representation illustrating the operating principle of the device represented in FIG. 1.

In the same time, from address 512 onwards, the counter CR addresses a position P'ij of a memory Mi (FIG. 2). To each point $P'_{11}$ to $P'_{nm}$ of this memory Mi is made correspond a position $P_{11}$ to $P_{nm}$ of the object examined O so that this "image" memory Mi can be subsequently drawn upon to provide an image of the object O.

For each of these points $P'_{11}$ to $P_{nm}$, a calculation is performed to determine the positions occupied in the field memory lines $L_1$ to $L_n$ by the reflected ultrasonic pulse, taking into account the shape of the field emitted, the digitization frequency, the speed of sound, the position of the object in relation to the probe. Thus, for the point Pij of the object which corresponds to the point P'ij of the image memory Mi, the positions occupied in the field memory MC are arranged according to a hyperbola indicated by the hatching.

If the probe 1 is in direct contact with the object, digitization can start at the same time as the transmission. When working with an acoustic relay, the start of the digitization can be deferred by a period of time equal to the outward and return journey in the relay.

The values read in the different memories (e.g. the values contained in the cells of the memory lines situated on the hyperbola H in relation to the point Pij) are added in an adding circuit S and sent to the selected position of the memory Mi (e.g. the position P'ij).

Thus, the circuit in FIG. 1 applies the following relations:

$$P'ij = \sum_{k=1}^{n} A_{k,l}, \text{ with } 1 = f_{i,j}(k) \qquad (1)$$

$A_{k,1}$ being the value of the sample stored in position 1 of the line $L_k$ of the field memory MC, and $f_{ij}(k)$ being the positions of the samples in lines $L_1$ to $L_n$ of the field memory, situated on the hyperbola corresponding to the point Pij.

As previously mentioned, the data contained in the memory Mi can be used in different ways.

They can be used to form an image on a conventional type viewing screen V.

These data can also be processed e.g. by logic circuits enabling the identification and recording of the type of faults detected in the case of a non-destructive test.

The addressing memory MA can be of the read-only type (ROM, PROM) programmed for once and for all. However, it is preferable, from the point of view of both the speed and flexibility of operation, to use a memory that can be reprogrammed once it has been installed, e.g. of the EPROM or RAM type.

The programming can then be performed at the time of starting up. The prior calculation can be made by a minicomputer as a function of the examination conditions and the probe model used. The data can also be precalculated and stored on disk or on a PROM. The results are then sequentially transferred to the memory MA by a conventional method. This transfer can be very rapid (a few seconds).

A method of calculating the addresses in the addressing memory MA will now be described in reference to FIG. 2.

Let us take a point Pij situated at a distance d from the probe vertically above the detection unit Di, to which point Pij is made correspond a position P'ij of the image memory Mi, and therefore an address supplied by the counter CR.

Let x be the distance separating the probe 1 from the unit under consideration, e.g. $D_2$, from the unit Di vertically above the point Pij, and let c be the speed of sound in the object medium.

If we suppose that the wave emitted by the probe 1 is plane and propagates perpendicularly to the surface of the probe 1, the amount of time t(x) taken by a pulse to reach the detection unit $D_2$ after reflection on the point Pij, is equal to the amount of time taken by the wave emitted to reach Pij, i.e. d/c+ the time taken by the wave between Pij and the unit $D_2$, i.e. (the square root of $(x^2+d^2)$)/c:

$$t(x) = \frac{d + \sqrt{x^2 + d^2}}{c} \quad (2)$$

If the writing frequency is designated by f and if the write operation starts at the same time as the transmission, the reflected signal will be stored in the cell of the field memory MC situated on the X-axis at the position f.t(x).

It is the value f.t(x) that will be entered into the memory MA for use during the read operation.

If the wave does not propagate perpendicularly to the probe (sampling at a slanted incidence) or if the wave is not plane (circular wave in the case of sectoral sampling), the calculation will be carried out in a very similar manner, the only change being the time taken by the wave to reach a point Pij. This amount of time will not only depend on d but also on the lateral position of the point Pij in relation to the probe 1. If the wave is slanted, the amount of time will vary linearly as a function of the lateral position Xp, the time taken by the wave emitted to reach the point Pij being equal to:

$$\frac{d \cdot \cos\theta + Xp \cdot \sin\theta}{c} \quad (3)$$

θ being the angle of the beam emitted in relation to the normal line of the probe 1.

Should the waves generated by the probe 1 be continuous or semi-continuous or should these waves be in the shape of a wave train of sufficient duration to cover the entire object, each point will give rise to a reflected wave of duration such that it will be memorized in virtually every position of the lines of the memories MC, and the data corresponding to the different points will be superposed on one another.

It may then be considered that one "slice" of these memories will contain all the data corresponding to the object, provided this slice is sufficiently "thick" to contain the largest of the hyperbolae.

The reading of this single slice will therefore be theoretically sufficient to recreate the image of the object.

This reading can be performed by gradually modifying the shape of the read hyperbolae, or by "focusing" on an area situated at a given distance.

The signal must then be digitized on a higher number of levels in order to enable good discrimination of the various data to be obtained.

It might also be envisaged, in order to simplify the electronics, that the memories MC be addressed sequentially during the write operation, rereading always being performed in parallel (in which case only one preamplifier and only one analog-to-digital converter are required).

Speed of acquisition is then notably decreased, but the resolution remains high. This solution can be of interest when speed is not a priority. It is also possible to envisage combinations of these two solutions: parallel writing in memory groups, these groups being addressed sequentially.

In the example described above, the ultrasonic signal is memorized prior to detection, therefore at the high frequency level. The sampling frequency must be equal to at least three times the ultrasonic frequency, e.g. 10 MHz for a 3-MHz ultrasonic wave.

Thus, when wishing to sound a depth of 20 cm in steel, the maximum duration of the outward and return journey is equal to approximately 60 μs at a speed of 6 mm/μs, i.e. 600 points sampled per line.

For a 100-line image, it will be necessary to compute 600×100=60,000 points. In this instance, the computation is merely a memory read operation followed by an addition.

With modern circuits, this operation can be performed in 1/100ths of a microsecond. The entire image can thus be computed in 60,000/100=600 microseconds.

It will have taken 60 microseconds to memorize the field, and the total acquisition time for an image will therefore be equal to 660 microseconds, with an image rate that can be in excess of 1000 Hz.

Should this rate prove insufficient, it can be increased in several ways:

a) division of the field memory into several sub-memories read in parallel;

b) selection and processing only of the memory zone containing the useful data.

It should be noted that the ultrasonic wave is often in the form of a brief pulse comprising several alternations. It may then be advantageous to use several read hyperbolae intercepting these alternations. If the pulse is short and only comprises one complete alternation, a hyperbola can be used to reread the positive alternation and at a distance corresponding to a half-period to reread the negative alternation. If Pp and Pm are the values obtained after these rereading operations, the value P=Pp−Pm will be recorded. This solution can enhance both the signal-to-noise ratio and the resolution of the system. The two readings can be conducted successively, to the detriment of speed, or in parallel using two memory groups.

The method according to the invention has numerous advantages over sequential methods.

Speed: A sizable area is explored with every shot, e.g. 100×5 mm, compared with 3×3 mm using the sequential method.

The speed of examination can be multiplied by 50 or 100 in relation to the sequential method, which is a very substantial increase.

The speed of the system makes it possible to use numerous applications such as three-dimensional imagery or Doppler imagery.

Three-dimensional imagery can be easily obtained if a matrix probe is used, though the electronics are very cumbersome since a conventional matrix probe comprises a large number of elements. However, the number of elements can be substantially reduced by randomly distributing these elements over the surface of the probe, thus authorizing a greater spacing apart of the elements without spurious lobes becoming too important. With a linear probe, a series of planes can be rapidly recorded by moving the cutting plane between each two shots. At a rate of 100 Hz, one thousand cutting planes can be memorized in 1/10th of a second. The memories can then be used to obtain a three-dimensional view or a cutaway view in any plane whatsoever.

As regards Doppler imagery, application thereof to Doppler imagery results from the fact that successive images can be compared. As the high-frequency signal is memorized, very small differences between two images can be detected (e.g. by subtraction) and shown up.

Resolution: The system operates with a very high numerical aperture. In practice, the spatial resolution is only limited by the bigger of two values, namely wavelength or dimension of an element. Thus, in the example quoted, the bigger of these two values is the wavelength, i.e. 2 mm. With a frequency of 10 MHz, the bigger of these two values would be the dimension of the element, in this instance 1 mm.

Reproducibility: The sensitivity of the system varies very little as a function of the position of an obstacle under the probe, and the field is emitted in the form of a plane wave. Moreover, sensitivity variations as a function of the position can be calculated, and therefore corrected, as the exact position of each obstacle in relation to the probe is known.

The system can operate with transmission wave edges of any shape (plane, slanted plane, cylindrical). In each case, the read hyperbolae form need only be computed as a function of their position. However, it so happens that when the number of reflecting points in the object O is much higher than the number of detection elements Di, and therefore than the number of lines Li in the field memory MC, artifacts can appear as the reflected field is then under-sampled and a non-zero value can be obtained at points corresponding to empty zones of the object O.

Figure 3:
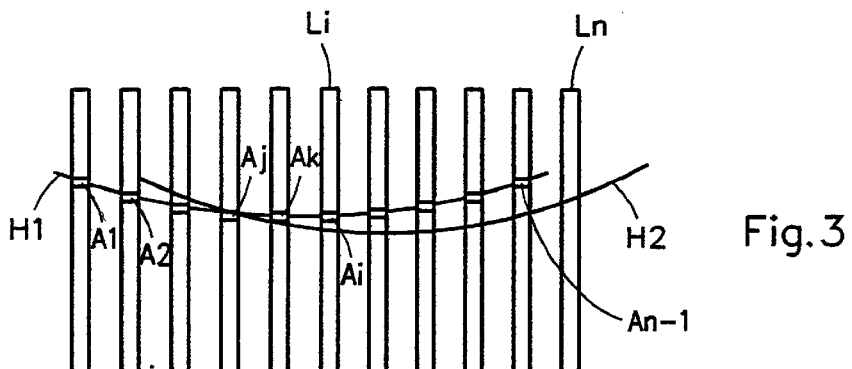
FIG. 3 schematically represents the field memory and the hyperbolic distribution within this memory of the echoes received by the detection elements.

Thus, as shown in FIG. 3, the point Pij of the object O reverberates a hyperbolic wave that is then found at the locations Ai (i being a variant of 1 to n–1) in the different lines Li of the field memory MC. If the read hyperbola H1 coincides with the hyperbola Ai written in the field memory, the value of the corresponding image point, which is equal to the sum of the values read in this memory, is at the maximum.

If we now consider a point of the object O which does not reverberate the wave because it is situated in an empty zone, the corresponding read hyperbola can intercept values of another read hyperbola corresponding to a wave reverberated by a point of the object. Thus, in FIG. 3, the hyperbola H2 intercepts the hyperbola H1 at points Aj and Ak. The value which is calculated for the point of an empty zone of the object, corresponding to the hyperbola H2, is therefore not nil. In the image memory Mi we thus obtain spurious points of low amplitude which reduce the quality of the image thus formed.

To remedy this drawback, the receiving units of the probe 1 can be more numerous and brought closer to one another, and the sampling frequency thereof can be increased. However, this solution then becomes a very costly one, making the use of matrix probes unrealistic.

According to the invention, all that needs to be done is to apply a correction factor to the value obtained at output of the adding circuit S, the correction factor varying as a function of a factor of coherence equal to the relation between the number Nr of non-zero values read in the lines Li of the field memory MC intercepted by the corresponding read hyperbola and the theoretical maximum number Nt which corresponds to the number of field memory cells intercepted by the read hyperbola. Theoretically, the value of this factor of coherence is one. However, in practice, certain obstacles of small dimension or occupying a particular position can reverberate weaker waves, in which case the factor of coherence can be lower than 1.

Figure 4:
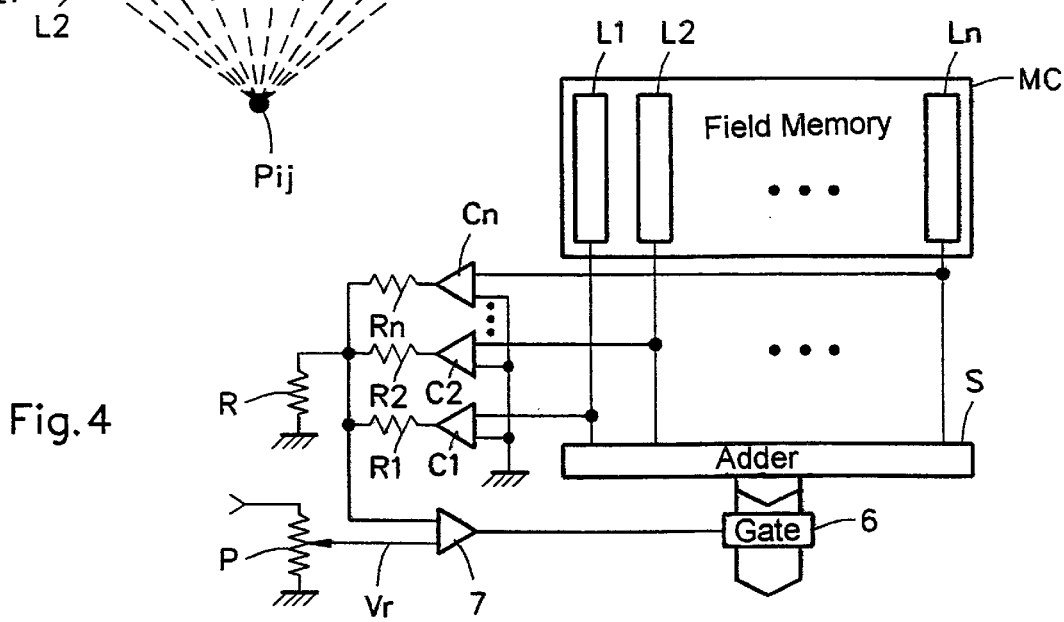
FIG. 4 illustrates another embodiment of the device represented in FIG. 1.

FIG. 4 shows another embodiment of the circuit represented in FIG. 1 which enables this principle to be applied. In this figure, comparators C1, C2, Cn are respectively connected to the link busses between the lines Li of the field memory and the adding circuit S in order to determine whether or not the values read are nil. To this end, one or more of the lesser significant bits of the values read can be neglected. The comparator outputs are applied to an analog summing integrator with resistors R1, R2, Rn. The output voltage of the summing integrator is this proportional to the number Nr of lines Li of field memory MC containing data that is not nil or not in the vicinity of nil. This output voltage is applied to the input of another comparator 7 of which the other input is connected to a reference voltage source Vr that can be adjusted by means of a potentiometer P. The output of this comparator 7 controls a gate 6 which may or may not validate the output of the adding circuit S towards the user circuit, e.g. the image memory Mi shown in FIG. 1. Thus, when the output voltage of the summing integrator equipped with resistors exceeds the reference voltage Vr, the comparator 7 provides a voltage which releases the gate 6.

The reference voltage Vr can vary as a function of the position of the corresponding point of the object O in relation to the probe 1. It is therefore advantageous to vary this voltage, e.g. by programming it, as a function of the position of the point being analyzed. Thus, this voltage can vary as a function of the theoretical maximum number Nt of lines Li of the field memory that should contain a non-zero value for each point of the object O.

In practice, a reference voltage value Vr chosen equal to from 0.6 to 0.8 times Nt is a good compromise.

As another preferred embodiment, the all-or-nothing threshold device constituted by the comparator 7 and the gate 6 can be replaced by a device which applies a more gradual correction to the output of the adding circuit S as a function the ratio Nr/Nt.

Figure 5:
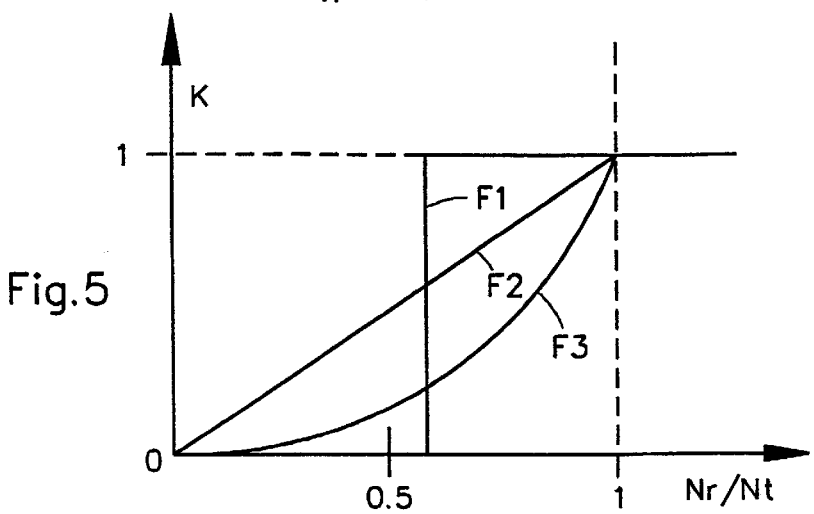
FIG. 5 represents examples of curves specifying the value of the correction factor that can be applied to the values obtained by the method according to the invention, as a function of the relation between the real and theoretical numbers of detectors receiving an echo from a given point.

FIG. 5 shows several possible curves stipulating the value of the correction factor K to be applied as a function of the ratio Nr/Nt. Curve F1 corresponds to the circuit represented in FIG. 4. Curve F2 illustrates the case where the factor of correction K is proportional to the ratio Nr/Nt, and curve F3 corresponds to the case where this factor K varies exponentially as a function of the ratio Nr/Nt.

To obtain such corrections, the comparator 7 and the gate 6 need only be replaced by a circuit with a transfer function taking into account the values Nr and Nt.

The analog circuit just described can, of course, be replaced by a completely digital circuit.

It should be noted that the acquisition speed depends on the rate of the sampling pulses emitted by the probe 1 in the direction of the object O to be analyzed, this rate being itself limited by the duration of the outward and return journey of the waves emitted and reverberated by the obstacles furthest from the object O.

Thus, in the case of underwater sounding aimed at detecting objects far away (several kilometers), the duration of the outward and return trip can be as long as several seconds.

FIGS. 6 and 7 illustrate this phenomenon. In FIG. 6, the probe 1 comprising the reception elements D1 has been represented, said probe transmitting towards an object notably comprising two points P1 and P2 which reverberate an echo towards the probe 1. In correspondence with these elements is shown the curve as a function of the timing of the pulses transmitted and received by the element Di of the probe 1. To the pulse transmitted E1 corresponds the pulses received R11 and R12 respectively retransmitted by the points P1 and P2. If the following pulse E2 is transmitted by the probe before the pulse R12 sent back by the point P2 is received by the probe, this pulse P12 will mix with the pulses, e.g. R21, sent back by the object, particularly by the point P1, after the pulse E2.

It is therefore necessary to wait until the waves retransmitted by all the points of the object have indeed returned before emitting the following pulse, otherwise the echoes from several successive pulses risk being mixed together at the level of the reception elements Di.

In fact, the solution described enables this phenomenon to be overcome. As explained above, each retransmitting point on the object to be analyzed sends back a hyperbola-shaped wave which is subsequently found in the field memory MC.

FIG. 7 represents the lines Li of the field memory MC over which have been superimposed the hyperbolic waves H1 and H2 respectively reverberated by the points P1 and P2 and corresponding respectively to the pulses R21 and R12 in FIG. 6. These hyperbolae can be seen to have a very different curve. The invention uses this phenomenon to multiply the transmission rate, bearing in mind that to each point on the object O to be analyzed corresponds a single read hyperbola of the field memory, irrespective of the position of the point in the object.

This arrangement is particularly advantageous when the wave travel time is long and the number of echoes received is limited, which is the case e.g. in underwater sounding.

Of course, in the case of a matrix probe, the field memory addresses containing the values received by the elements detecting the wave sent back by a point of the object are distributed over a hyperbolic surface of revolution.

The device embodying the invention thus enables the volume analysis of the structure to be carried out at a high acquisition rate.

To further enhance this solution, it should be noted that in order to maintain good resolution, each element must have a very open radiation pattern, which usually implies that the detection elements Di of the probe 1 be of very small size, this dimension being preferably lower than the wavelength. If there are few elements, the total reception area of the probe 1 will also be small, whence a loss of sensitivity which can be very disadvantageous. To remedy this drawback, the invention proposes to use detection elements of dimension in excess of one wavelength, associating thereto miniature lenses or spherical cap-shaped elements in order to increase the aperture of the elements without modifying their dimension or sensitivity.

Thus, as represented in FIG. 8a, the detection elements Di generally have an aperture α of less than 20°. If a lens or spherical cap 11 is added thereto, as represented in FIG. 8b, this aperture α' can be significantly increased (over 120°).

This solution makes it possible to manufacture matrix probes at a reasonable cost. FIG. 9 shows a sample embodiment of such a probe according to the invention, this probe 1' having a emission surface of rectangular shape, and a limited number of transmission and detection elements Di randomly distributed over the emission surface.

Furthermore, when wishing to cover an extended sector (e.g. 60°) with acceptable resolution and sufficient detection sensitivity, emission must be in the entire sector and at a high transmission power. The solution will then be to perform a scan while emitting successive shots. However, in the case of long-distance underwater sounding, this leads to a very lengthy acquisition time for the scanning, which is a serious handicap when attempting to detect fast-moving targets.

However, current long-range probes use ultrasonic transducer matrices to emit a narrow beam and bring about angular displacement of this beam by acting on the phase shifts between the different elements of the probe.

The solution according to the invention consists in performing successive emissions of a narrow beam and in modifying the orientation of said beam between each emission so as to cover the entire sector in question.

At reception, all the signals detected respectively by the probe elements are digitized and stored, as described above, in the respective lines of the field memory.

As the sounding distance is very long in relation to the dimensions of the probe, the data corresponding to an obstacle are distributed in the field memory along arcs of hyperbolae which can be assimilated with straight lines.

It should also be noted that the slant of these straight lines depends on the orientation of the beam emitted and with which the corresponding obstacle was detected. It is thus possible to accurately identify, when rereading the field memory, the direction in which an obstacle was detected.

Conventional probes are directional at both transmission and reception levels. With such probes, it is therefore necessary to wait until all the echoes of the pulse emitted in a given direction have returned, before changing the direction of the probe. However, the probe described above emits a narrow beam but can recover echoes in a very narrow angle. In these conditions, the emissions can be repeated at a very high rate that will be independent of the time required for the outward and return journey of the pulses. Let us take the example of a sonar of kilometric range operating at a frequency of 100 kHz, with a probe 3 meters wide and 50 cm high and comprising 200 transducer elements. Such a probe emits a 1/200th radian beam, i.e. 0.6° in the horizontal plane and 3.6° in the vertical plane. As previously indicated, acoustic lenses can be placed in front of each element to increase the divergence thereof.

With such a sonar, the beam emitted can be oriented at an angle varying by $-\Delta\theta$ to $+\Delta\theta°$ in relation to an axis perpendicular to the probe, by electronic phase shifting of the signals emitted by the probe elements. If, after each 1-ms emission the orientation of the beam is modified by 0.5°, i.e. a scanning speed of $V_b=0.5°/ms$, the sector to be explored can be completely scanned in 180 ms, when $\Delta\theta$ is equal to e.g. 45°.

However, it is necessary to wait until all the echoes have been received before proceeding to carry out another scanning. Thus, for a range d=1 km in a marine environment, this waiting time t has a maximum value of $2\times d/V_t$, $V_t$ being the speed of propagation of sound in a marine environment and having a value of 1500 m/s, i.e. 1.33 s. Allowing for a margin of safety, a scan can therefore be performed every 2 s.

Let us suppose that two obstacles have been detected, the first at a distance r1=600 m at an angle θ1=−40° and the second at a distance r2=500 m at an angle θ2=+40°. In relation to a zero point of time corresponding to the start of the scanning, the first obstacle will have been encountered by a pulse emitted at the instant $t1=(\theta1+\Delta\theta)/V_b=10$ ms, whereas the second obstacle will have been encountered by a pulse emitted at the instant $t2=(\theta2+\Delta\theta)/V_b=170$ ms.

The amount of time taken by the reflected pulses to reach the center of the probe will be respectively equal to $2\times r1/V_t=0.8$ s and $2\times r2/V_t=0.666$ s. We thus obtain the following instants of arrival:

$$t'1 = \frac{(\theta1 + \Delta\theta)}{V_b} + 2\times \frac{r1}{V_t} = 0,81\ s,\ et \quad (4)$$

$$t'2 = \frac{(\theta2 + \Delta\theta)}{V_b} + 2\times \frac{r2}{V_t} = 0,83\ s. \quad (5)$$

In this particular case it can be seen that the echo corresponding to the obstacle furthest away arrives before the echo corresponding to the nearest obstacle.

During processing of the echoes received by the computing circuit, the field memory is explored by series of straight lines sloped at angles corresponding to the different transmission angles. When a reading line coincides with a recorded line, the corresponding information is written in the image memory Mi. The coordinates of the point inscribed in the image memory thus vary as a function of the angle of slope of the line, i.e. the direction of the obstacle, and of the position of the line in the memory, rectified by the time shift corresponding to the instant of transmission in that direction.

The value of a point P'r,θ corresponding to a point Pr,θ of the environment explored is thus obtained as follows:

$$P'r, \theta = \sum_{k=1}^{n} A_{k,l},\ \text{with}\ 1 = k\times\cos\theta + C\times\left(\frac{2r}{V_t} + \frac{\theta}{V_b}\right) \quad (6)$$

$A_{k,1}$ being the value of the sample stocked in position 1 of the line $L_k$ of the field memory MC, and C being a constant dependent on the sampling frequency of the converter CA.

Due to the fact that the relation between 1 and k is a simple one, the addresses of the samples stocked in the field memory MC, to be added up to obtain the value of a point in the image memory Mi, can be computed as the image is constituted in the image memory Mi by using tables of constants specifying, for each shooting angle $\theta$ and each line $1_k$ of the field memory, the value of $k \times \cos\theta$.

The image contained in the image memory can be displayed in sectoral form (i.e. in polar coordinates: $r,\theta$), or be subjected to a conversion processing in order to be displayed as Cartesian coordinates.

The invention also enables the solving of the problems that arise in the case of short-distance sounding (e.g. 100 mm).

When the probe is of sizable dimension (100-mm strip), the ultrasonic field is very disturbed in the vicinity of the transmitting surface and the average intensity is reduced, which reduced the sensitivity of the detection. This phenomenon can be corrected by applying an amplitude weighting to the different elements, but this solution is still imperfect Furthermore, when there is a large number of obstacles, e.g. in the case of medical echo scanning or echography, artifacts can appear on the image obtained.

One solution to this problem consists in reducing the transmitting surface by switching of the probe elements at the transmission, and by shifting the position of this surface for each transmission. This will thus produce the equivalent of a mobile exploration beam, but the rate of acquisition will then be considerably reduced. This drawback can be attenuated by simultaneously emitting several beams sufficiently spaced apart so as not to interfere with one another, in such a way as to e.g. scan the entire object within a small number of transmissions.

For instance, if a beam 10 mm wide is used with a probe 1000 mm wide, it will take 20 successive single-beam shots with a 50% overlap between the beams. If five beams spaced 20 mm apart are emitted simultaneously, four shots will be sufficient, though the rate of constitution of the images will be divided by four.

The invention enables this result to be improved upon. To this end, it is based on the following observations:

In medical echography for instance, the shooting rate can be considerably higher than the image processing rate. Thus, to examine a structure of up to 100 mm deep, the maximum time of the outward and return journey of a pulse is $2\times0.1$ m/1500 m/s, i.e. 0.13 ms. In the human body, the absorption of ultrasonic waves is very high and reverberation is practically non-existent. The shooting can thus be carried out at a rate of 5000 Hz, whereas the rate of reconstitution of the image cannot exceed approximately 1000 Hz with current techniques.

It is therefore possible, using a field memory MC of greater capacity, to record the samples obtained subsequent to several successive shots (e.g. four) in a respective zone of this memory, and to perform the processing subsequently. Each of these field memory zones only contains the data relating to one quarter of the image to be reconstituted. Accordingly, they can be processed much more rapidly (four times faster in the case of four successive shots).

In this example, an acquisition and processing cycle can be carried out in 2 ms, which corresponds to a frequency of 500 Hz which is usually sufficient.

This rate may however be doubled by using two field memories MC or one field memory of double capacity, in order to be able to memorize the samples in a memory or part thereof, while the other memory or other part of this memory is used by the processing circuits.

I claim:

1. A method for exploring and analyzing a structure of a medium by means of a set of a plurality of detection elements independent from one another, for detecting waves coming from points of said medium, said method having a measurement phase comprising the successive steps of:

transmitting at least one incident wave in said structure;

receiving waves coming from the structure encountered by the incident wave inside said medium, by each of said detection elements;

digitizing signals supplied by said detection elements into digitized data and storing said data in a field memory having a two-dimensional structure comprising a plurality of rows and columns, the data corresponding to the waves detected by each of said detection elements being stored in a respective column of said field memory; and for each point of said medium reading said field memory and adding all data contained in said field memory at addresses associated to said point and stored in an addressing memory, a value representative of the importance of the wave coming from said point being obtained by multiplying the added data by a correction factor, said method having an initialization phase performed prior to said measurement phase and comprising the steps of:

for each point of said medium, determining all addresses of said field memory containing the data corresponding to waves coming from said point and detected by said detection elements, as a function of a position of said point with regard to respective positions of said detection elements, and storing said addresses for each point in said addressing memory.

2. The method as claimed in claim 1, wherein all the rows of the field memory are read in parallel, and the values representative of the importance of the waves coming respectively from said points of said medium being stored in an image memory comprising a plurality of memory locations to each of which corresponds a read addressing law of said field memory, said read addressing law having parameters depending on the position of the memory location of said image memory.

3. The method as claimed in claim 2, wherein the correction factor for a point varies as a function of a ratio of a number of values read for said point in the field memory and which are in excess of a predetermined threshold, and the total number of values read for said point in said field memory.

4. The method as claimed in claim 3, wherein the correction factor is nil when below a certain threshold as a function of the ratio and has a value of 1 when it is above said threshold.

5. The method as claimed in claim 3, wherein the correction factor is proportional to said ratio.

6. The method as claimed in claim 3, wherein the correction factor varies exponentially as a function of said ratio.

7. The method as claimed in claim 2, wherein several read addressing laws are associated with each memory location of the image memory.

8. The method as claimed in claim 1, wherein said incident waves are emitted in the form of pulses.

9. The method as claimed in claim 1, wherein the incident waves are emitted in the form of wave trains or of a continuous transmission, the addressing law then being chosen so as to show up points of said medium situated at a predetermined distance from said detection elements.

10. The method as claimed in claim 1, wherein the emission of the incident waves and the reception of the waves reverberated by said medium are performed by same means.

11. The method as claimed in claim 9, wherein the emission of the incident waves and the reception of the waves reverberated by the environment are performed by separate means.

12. The method as claimed in claim 1, wherein the incident waves have plane wavefronts.

13. The method as claimed in claim 1, wherein the incident waves are composed of directional and/or focused beams which do not overlap, said beams being moved during successive emissions in order to cover entire structure of said medium.

14. The method as claimed in claim 1, wherein said incident waves are generated by means of a linear network of independent transmission/reception units.

15. The method as claimed in claim 1, wherein said incident waves are generated by means of transmission/reception units arranged according to a matrix configuration.

16. The method as claimed in claim 1, wherein said incident waves are generated by transmission/reception units arranged randomly.

17. The method as claimed in claim 1, further comprising successive transmissions of incident waves in different directions corresponding to respective angles of transmission, at a high rate independent of a duration of an outward and return journey of a wave between the detecting elements and said medium encountered by the wave, each point of said medium susceptible of being hit by a pulse corresponding to a separate set of addresses in the field memory containing a value representing the importance of the wave coming from said point.

18. The method as claimed in claim 2, wherein said addressing law is a hyperbolic or pseudo-hyperbolic law.

19. The method as claimed in claim 2, wherein the incident waves are emitted towards an obstacle situated at a distance far greater than the dimensions of the set of said detection elements, so that said addressing law can be assimilated with a straight line having a slope depending on the angular position of the obstacle in relation to the set of detection elements.

20. The method as claimed in claim 1, wherein the detection elements are also emitters, the method comprising distributing said detection elements into separate groups which are activated for transmission one after the other during a set of successive transmissions, all the detection elements being active for reception, information received by the detection elements being stored in separate zones of the field memory.

21. A device for exploring and analyzing a structure of a medium comprising a probe composed of a plurality of independent transmission/reception units each connected to a wave generator, via two conduction threshold diodes mounted head-to-foot, and to an analog-to-digital converter having an output connected to a write input of a field memory in which reading is controlled by an addressing memory driven by a clock via a counter, the read output of the field memory being connected to an adder having an output connected, via a correction means, to a write input of an image memory driven by said counter, the correction means being driven by a device for counting the number of values above a predetermined threshold, read in the field memory and added together.

22. The device as claimed in claim 21, wherein the transmission/reception units have dimensions greater than a wavelength of the wave emitted and are each fitted with a means for increasing their aperture.

23. The device as claimed in claim 22, wherein the means for increasing the aperture of the transmission/reception units comprises miniature lenses or spherical caps.

24. The device as claimed in claim 22, wherein the transmission/reception units are arranged according to a matrix configuration, the reception units being distributed randomly within said configuration.

25. The device as claimed in claim 22, further comprising two field memory zones which are alternately written in and read so as to double a rate of production of images in the image memory.

* * * * *